USO12403309B2

(12) United States Patent
Bennett

(10) Patent No.: US 12,403,309 B2
(45) Date of Patent: Sep. 2, 2025

(54) TRANSCUTANEOUS POWER AND DATA COMMUNICATION LINK

(71) Applicant: Cochlear Limited, Macquarie University (AU)

(72) Inventor: Robert Graham Bennett, St Peters (AU)

(73) Assignee: Cochlear Limited, Macquarie University (AU)

( * ) Notice: Subject to any disclaimer, the term of this patent is extended or adjusted under 35 U.S.C. 154(b) by 1125 days.

(21) Appl. No.: 17/294,085

(22) PCT Filed: Jul. 10, 2020

(86) PCT No.: PCT/IB2020/056528
§ 371 (c)(1),
(2) Date: May 14, 2021

(87) PCT Pub. No.: WO2021/009646
PCT Pub. Date: Jan. 21, 2021

(65) Prior Publication Data
US 2022/0072306 A1 Mar. 10, 2022

Related U.S. Application Data

(60) Provisional application No. 62/874,117, filed on Jul. 15, 2019.

(51) Int. Cl.
*A61N 1/36* (2006.01)
*A61N 1/372* (2006.01)
(Continued)

(52) U.S. Cl.
CPC ..... *A61N 1/36038* (2017.08); *A61N 1/37252* (2013.01); *A61N 1/3787* (2013.01);
(Continued)

(58) Field of Classification Search
CPC .... F02B 2075/025; F02B 63/00; F02B 75/16; F01P 1/02; A61N 1/36038;
(Continued)

(56) References Cited

U.S. PATENT DOCUMENTS

2009/0085408 A1 4/2009 Bruhn
2012/0274270 A1 11/2012 Dinsmoor et al.
(Continued)

FOREIGN PATENT DOCUMENTS

CN 101859484 A 10/2010
CN 108781094 A 11/2018
(Continued)

OTHER PUBLICATIONS

International Search Report and Written Opinion in counterpart International Application No. PCT/IB2020/056528, mailed Oct. 13, 2020, 13 pages.
(Continued)

*Primary Examiner* — Amanda K Hulbert
(74) *Attorney, Agent, or Firm* — Edell, Shapiro & Finnan, LLC

(57) ABSTRACT

Presented herein are techniques for transcutaneously transferring power and data from an external component to an implantable component of an implantable medical device. In accordance with embodiments presented herein, the implantable component comprises an implantable resonant circuit, while the external component comprises an external resonant circuit. The external component also comprises external radio-frequency (RF) interface circuitry configured to drive the external resonant circuit at a first frequency in order to transfer power to the implantable resonant circuit, and to drive the external resonant circuit at a second frequency, which is different from the first frequency, in order to transfer data to the implantable resonant circuit.

15 Claims, 10 Drawing Sheets

(51) Int. Cl.
*A61N 1/378* (2006.01)
*H02J 50/12* (2016.01)
*H02J 50/20* (2016.01)

(52) U.S. Cl.
CPC .............. *H02J 50/12* (2016.02); *H02J 50/20* (2016.02); *H02J 2310/23* (2020.01)

(58) Field of Classification Search
CPC ............ A61N 1/37223; A61N 1/37252; A61N 1/3787; F02M 35/024; H02J 2310/23; H02J 50/12; H02J 50/20
See application file for complete search history.

(56) References Cited

U.S. PATENT DOCUMENTS

| 2015/0209591 A1 | 7/2015 | Meskens |
| 2016/0285300 A1 | 9/2016 | Summers et al. |
| 2017/0127196 A1* | 5/2017 | Blum .................... H04R 25/554 |
| 2017/0141584 A1 | 5/2017 | DeVaul et al. |
| 2017/0246462 A1 | 8/2017 | Meskens |
| 2018/0239999 A1 | 8/2018 | Gayton |

FOREIGN PATENT DOCUMENTS

| JP | H04336801 A | 11/1992 |
| WO | 2017059540 A1 | 4/2017 |

OTHER PUBLICATIONS

Extended European Search Report in counterpart European Application No. 20840222.2-1202, mailed Aug. 8, 2023, 7 pages.

\* cited by examiner

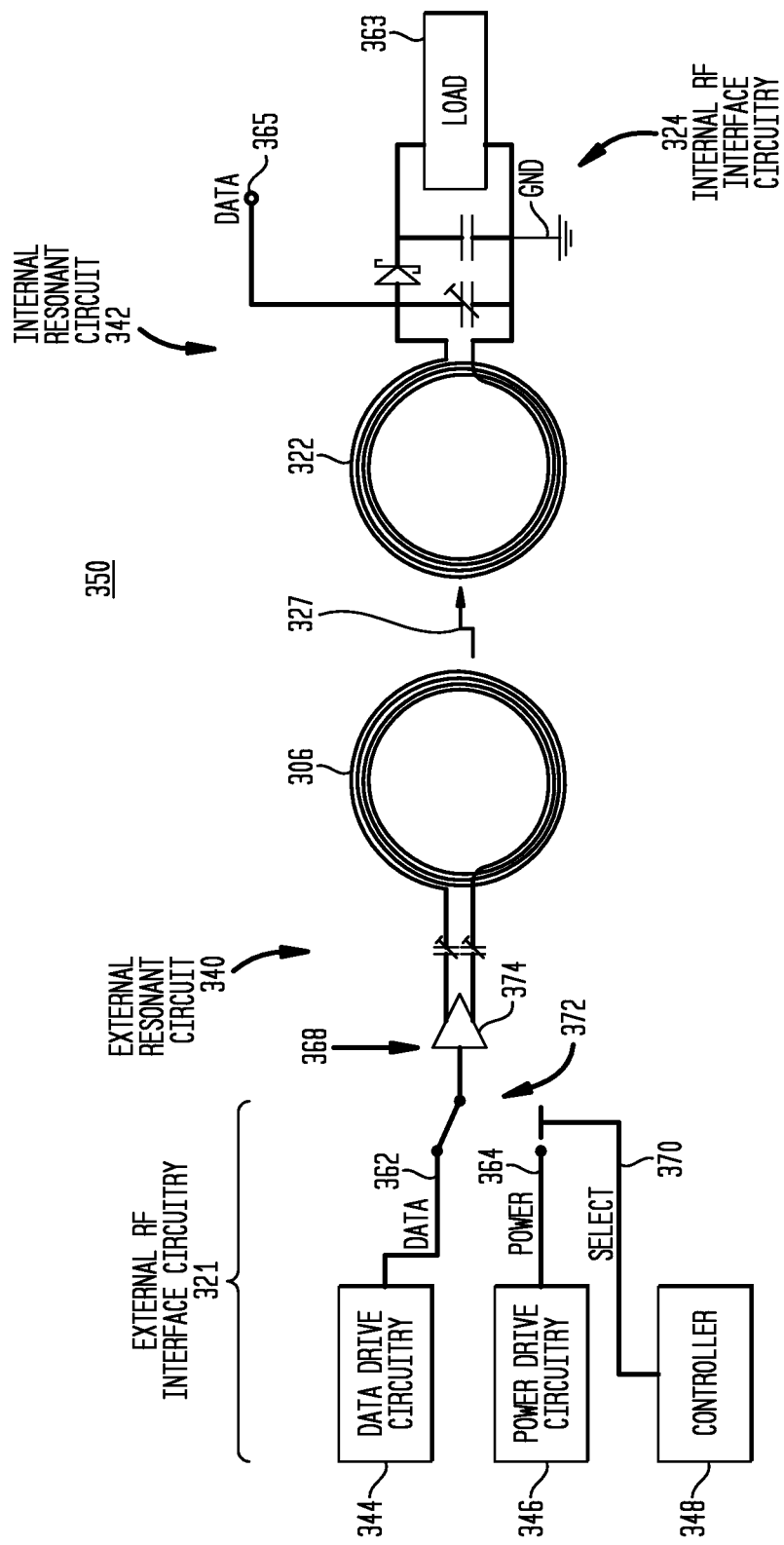

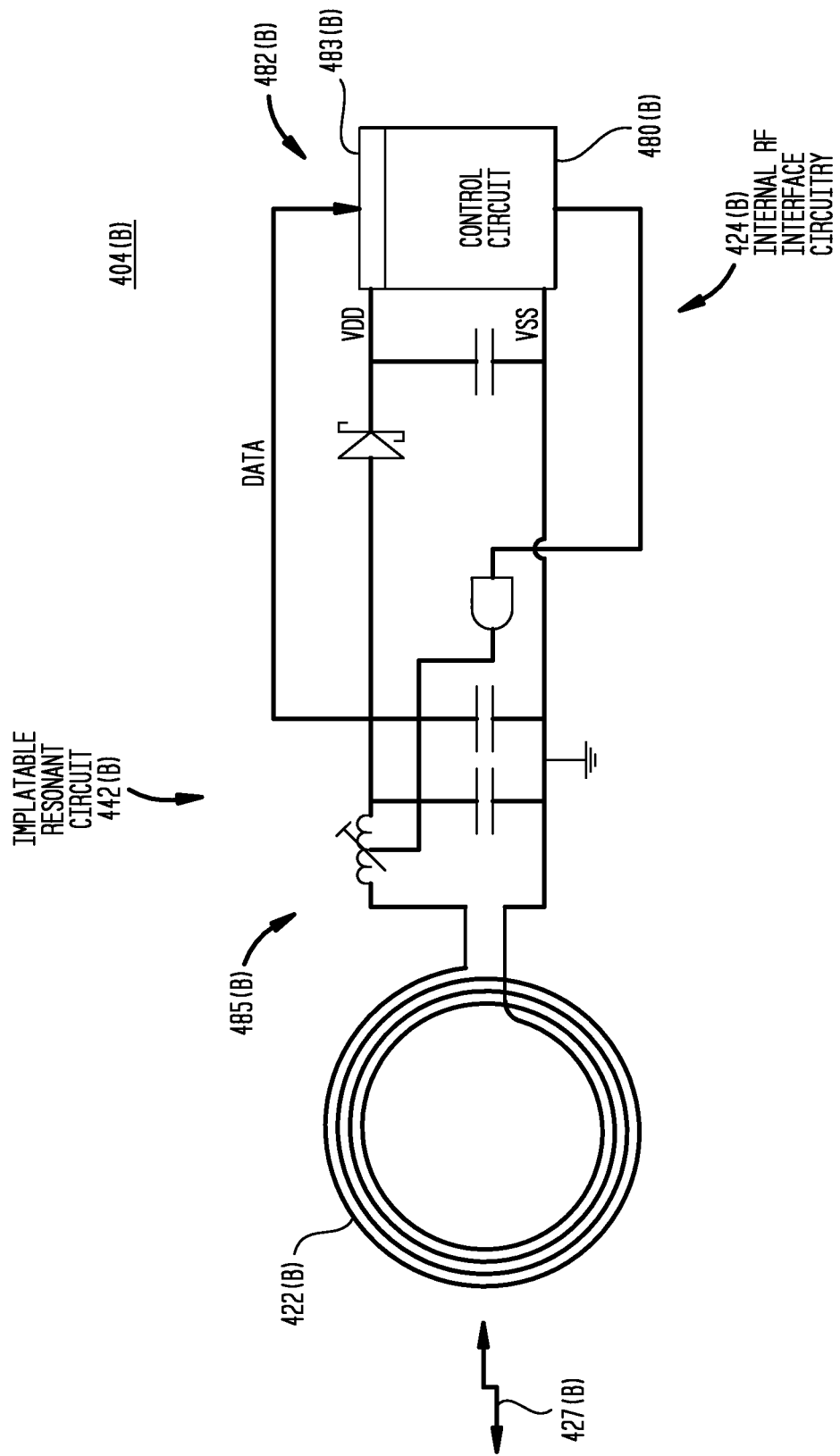

SENDING, VIA AN EXTERNAL RESONANT CIRCUIT OF AN EXTERNAL COMPONENT OF AN IMPLANTABLE MEDICAL DEVICE, POWER SIGNALS TO AN IMPLANTABLE RESONANT CIRCUIT OF THE IMPLANTABLE MEDICAL DEVICE, WHEREIN THE POWER SIGNALS HAVE A FIRST FREQUENCY — 692

SENDING, VIA THE EXTERNAL RESONANT CIRCUIT, DATA SIGNALS TO THE IMPLANTABLE RESONANT CIRCUIT, WHEREIN THE DATA SIGNALS HAVE A SECOND FREQUNECY AND WHEREIN A PHYSICAL ARRANGEMENT OF EACH OF THE IMPLANTABLE RESONANT CIRCUIT AND THE EXTERNAL RESONANT CIRCUIT DOES NOT CHANGE WHETHER SENDING THE POWER OR DATA SIGNALS TO THE IMPLANTABLE RESONANT CIRCUIT — 694

TRANSCUTANEOUS POWER AND DATA COMMUNICATION LINK

BACKGROUND

Field of the Invention

The present invention relates generally to transcutaneous communication links in implantable medical device systems.

Related Art

Medical device systems having one or more implantable components, generally referred to herein as implantable medical device systems, have provided a wide range of therapeutic benefits to recipients over recent decades. In particular, partially or fully-implantable medical device systems such as hearing prosthesis systems (e.g., systems that include bone conduction devices, mechanical stimulators, cochlear implants, etc.), implantable pacemakers, defibrillators, functional electrical stimulation systems, etc., have been successful in performing lifesaving and/or lifestyle enhancement functions for a number of years.

The types of implantable medical device systems and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device system.

SUMMARY

In one aspect an implantable medical device is provided. The implantable medical device comprises: an implantable resonant circuit comprising an implantable coil; an external resonant circuit comprising an external coil configured to transcutaneously transfer power and data to the implantable resonant circuit using separate power and data time slots, respectively; and external radio-frequency (RF) interface circuitry configured to drive the external resonant circuit at a first frequency during the power time slots and to drive the external resonant circuit at a second frequency during data time slots, wherein the second frequency is different from the first frequency.

In another aspect a method is provided. The method comprises: during a first set of time periods, driving an external resonant circuit comprising an external coil with power drive signals having a first center frequency to cause the external coil to transfer power to an implantable resonant circuit; and during a second set of time periods that are different from the first set of time periods, driving the external resonant circuit with data drive signals having a second center frequency to cause the external coil to transfer data to the implantable resonant circuit, wherein the second frequency is different from the first frequency, and wherein the external resonant circuit and the implantable resonant circuit each have an associated tuned frequency that remains the same during each of the first and second sets of time periods.

In another aspect an external component of an implantable medical device is provided. The external component comprises: an external coil configured to forming a transcutaneous communication link with an implantable resonant circuit; power drive circuitry configured to drive the external resonant circuit with power drive signals having a first center frequency to cause the external coil to transfer power to the implantable resonant circuit; and data drive circuitry configured to drive the external resonant circuit with data drive signals having a second center frequency to cause the external coil to transfer power to the implantable resonant circuit, wherein the first frequency provides a selected power coupling between the external resonant circuit and the implantable resonant circuit, and wherein the second frequency is frequency spaced from the first frequency by a selected frequency distance so as to provide a selected bandwidth for the transcutaneous communication link.

In another aspect a method is provided. The method comprises: sending, via an external resonant circuit of an external component of an implantable medical device, power signals to an implantable resonant circuit of the implantable medical device, wherein the power signals have a first frequency; and sending, via the external resonant circuit, data signals to the implantable resonant circuit, wherein the data signals have a second frequency, and wherein a physical arrangement of each of the implantable resonant circuit and the external resonant circuit remains fixed does not change during either of the power or data time slots.

BRIEF DESCRIPTION OF THE DRAWINGS

Embodiments of the present invention are described herein in conjunction with the accompanying drawings, in which:

FIG. 3 is schematic diagram illustrating a resonant system for use in the transcutaneous transfer of power and data, in accordance with certain embodiments presented herein.

FIG. 4B is a schematic diagram illustrating portion of an implantable component, in accordance with certain embodiments presented herein;

FIG. 6 is flowchart of another method, in accordance with certain embodiments presented herein.

DETAILED DESCRIPTION

Presented herein are techniques for transcutaneously transferring power and data from an external component to an implantable component of an implantable medical device. In accordance with embodiments presented herein, the implantable component comprises an implantable resonant circuit, while the external component comprises an external resonant circuit. The external component also comprises external radio-frequency (RF) interface circuitry configured to drive the external resonant circuit at a first frequency in order to transfer power to the implantable resonant circuit, and to drive the external resonant circuit at a second frequency, which is different from the first frequency, in order to transfer data to the implantable resonant circuit.

There are a number of different types of implantable medical device systems in which embodiments presented herein may be implemented. However, merely for ease of illustration, the techniques presented herein are primarily described with reference to one type of implantable medical device system, namely a cochlear implant. It is to be appreciated that the techniques presented herein may be used in any other partially or fully implantable medical devices now known or later developed, including other auditory prostheses, such as auditory brainstem stimulators, electro-acoustic hearing prostheses, acoustic hearing aids, bone conduction devices, middle ear prostheses, direct cochlear stimulators, bimodal hearing prostheses, etc. The techniques presented herein may also be used with balance prostheses (e.g., vestibular implants), retinal or other visual prosthesis/stimulators, occipital cortex implants, sensor systems, implantable pacemakers, drug delivery systems, defibrillators, catheters, seizure devices (e.g., devices for monitoring and/or treating epileptic events), sleep apnea devices, electroporation devices, spinal cord stimulators, deep brain stimulators, motor cortex stimulators, sacral nerve stimulators, pudendal nerve stimulators, vagus/vagal nerve stimulators, trigeminal nerve stimulators, diaphragm (phrenic) pacers, pain relief stimulators, other neural, neuromuscular, or functional stimulators, etc.

Figure 1A:
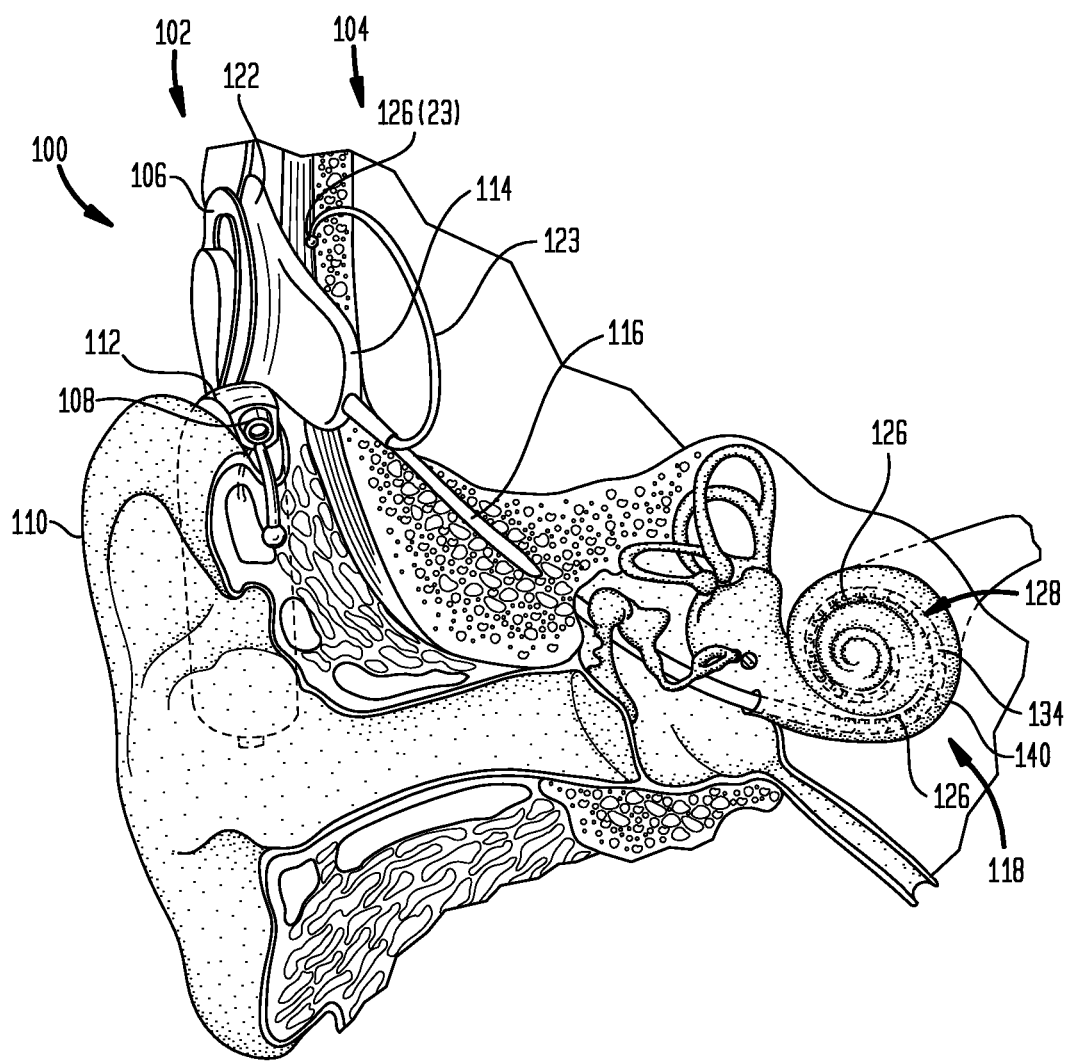
FIG. 1A is a schematic diagram illustrating a cochlear implant, in accordance with certain embodiments presented herein.
Figure 1B:
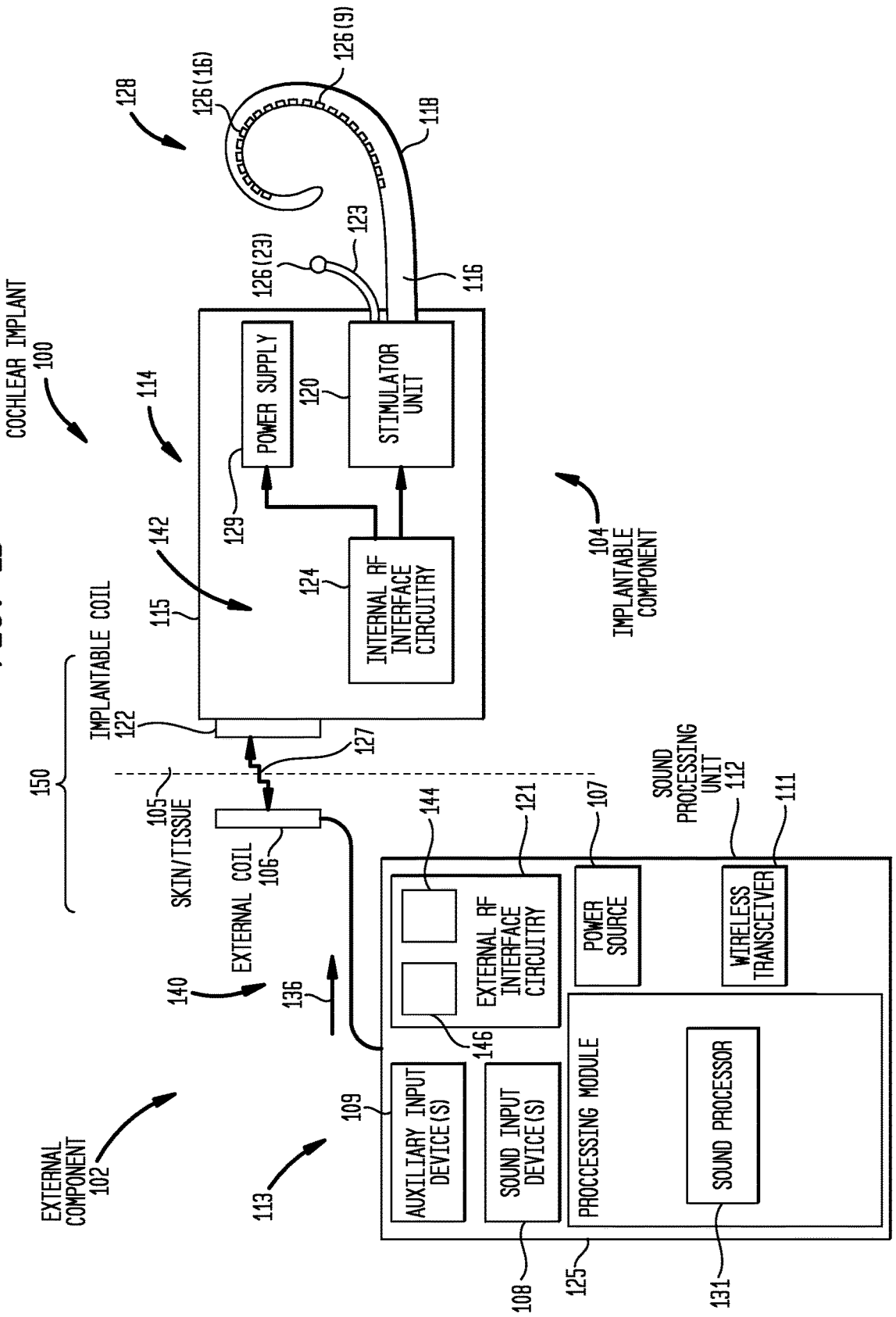
FIG. 1B is a block diagram of the cochlear implant of FIG. 1A.

FIG. 1A is a schematic diagram of an exemplary cochlear implant 100 in accordance with aspects presented herein, while FIG. 1B is a block diagram of the cochlear implant 100. For ease of illustration, FIGS. 1A and 1B will be described together.

The cochlear implant 100 comprises an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more input elements/devices 113 for receiving input signals at a sound processing unit 112. In this example, the one or more input devices 113 include sound input devices 108 (e.g., microphones positioned by auricle 110 of the recipient, telecoils, etc.) configured to capture/receive input signals, one or more auxiliary input devices 109 (e.g., audio ports, such as a Direct Audio Input (DAI), data ports, such as a Universal Serial Bus (USB) port, cable port, etc.), and a wireless transmitter/receiver (transceiver) 111, each located in, on, or near the sound processing unit 112.

The sound processing unit 112 also includes, for example, at least one battery 107, external radio-frequency (RF) interface circuitry 121, and a processing module 125. The processing module 125 may comprise a number of elements, including a sound processor 131. As described further below, the external RF interface circuitry 121 comprises data drive circuitry 144 and power drive circuitry 146 which are selectively activated/used for transcutaneous transmissions of data and power, respectively, to the implantable component 104.

In the examples of FIGS. 1A and 1B, the sound processing unit 112 is a behind-the-ear (BTE) sound processing unit configured to be attached to, and worn adjacent to, the recipient's ear. However, it is to be appreciated that embodiments of the present invention may be implemented by sound processing units having other arrangements, such as by an off-the-ear (OTE) sound processing unit (i.e., a component having a generally cylindrical shape and which is configured to be magnetically coupled to the recipient's head), etc., a mini or micro-BTE unit, an in-the-canal unit that is configured to be located in the recipient's ear canal, a body-worn sound processing unit, etc.

Returning to the example embodiment of FIGS. 1A and 1B, the implantable component 104 comprises an implant body (main module) 114, a lead region 116, and an intra-cochlear stimulating assembly 118, all configured to be implanted under the skin/tissue (tissue) 105 of the recipient. The implant body 114 generally comprises a hermetically-sealed housing 115 in which internal RF interface circuitry 124, a power supply 129 (e.g., one or more implantable batteries, one or more capacitors, etc.), and a stimulator unit 120 are disposed. The stimulator unit 120 comprises, among other elements, one or more current sources on an integrated circuit (IC).

The implant body 114 also includes an internal/implantable coil 122 that is generally external to the housing 115, but which is connected to the RF interface circuitry 124 via a hermetic feedthrough (not shown in FIG. 1B). It is to be appreciated that implantable component 104 and/or the external component 102 may include other components that, for ease of illustration, have been omitted from FIGS. 1A and 1B.

As noted, the cochlear implant 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil.

The operational alignment of the coils 106 and 122 enables the external component 102 to transfer power (e.g., for use in powering components of the implantable component) and data (e.g., for use in generating signal signals) to the implantable component 104 via a bidirectional "transcutaneous communication link" or "closely-coupled wireless link" 127 formed between the external coil 106 with the implantable coil 122. That is, due to the operational alignment, the data drive circuitry 144 in external RF interface circuitry 121 can be used to transfer data to the implantable component 104 via the closely-coupled wireless link 127. Similarly, the operational alignment of coils 106 and 122 enables the power drive circuitry 146 to transfer power signals (power) to the implantable component 104 via the closely-coupled wireless link 127. The power signals, when received by the internal RF interface circuitry 124, may be used to power the elements of implantable component 104 and/or used to provide power to the power supply 129.

In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

As noted above, sound processing unit 112 includes the processing module 125. The processing module 125 is configured to convert input audio signals into stimulation control data 136 for use in stimulating a first ear of a recipient (i.e., the processing module 125 is configured to perform sound processing on input audio signals received at the sound processing unit 112). Stated differently, the sound processor 131 (e.g., one or more processing elements implementing firmware, software, etc.) is configured to convert the captured input audio signals into stimulation control data 136 that represents stimulation signals for delivery to the recipient. The input audio signals that are processed and converted into stimulation control data may be audio signals received via the sound input devices 108, signals received via the auxiliary input devices 109, and/or signals received via the wireless transceiver 111.

In the embodiment of FIG. 1B, the stimulation control data 136 is provided to the external RF interface circuitry 121, where the data drive circuitry 144 transcutaneously transfers the stimulation control data 136 (e.g., in an encoded manner) to the implantable component 104 via external coil 106 and implantable coil 122. That is, the stimulation control data 136 is sent by the data drive circuitry 144 over the closely-coupled wireless link 127. The internal RF interface circuitry 124 is configured to receive the stimulation control data 136 via implantable coil 122 and to provide that data to the stimulator unit 120. The stimulator unit 120 is configured to utilize the stimulation control data 136 to generate stimulation signals (e.g., current signals) for delivery to the recipient's cochlea via the stimulating assembly 118. In this way, cochlear implant 100 electrically stimulates the recipient's auditory nerve cells, bypassing absent or defective hair cells that normally transduce acoustic vibrations into neural activity, in a manner that causes the recipient to perceive one or more components of the input audio signals.

More specifically, as noted above, stimulating assembly 118 is configured to be at least partially implanted in the recipient's cochlea 140. Stimulating assembly 118 includes a plurality of longitudinally spaced intra-cochlear electrical contacts (electrode contacts or electrodes) 126 that collectively form an electrode contact array 128 configured to, for example, deliver electrical stimulation signals (current signals) generated based on the stimulation control data 136 to the recipient's cochlea. In certain examples, the electrode contacts 126 may also be used to sink stimulation signals from the recipient's cochlea.

FIG. 1A illustrates a specific arrangement in which stimulating assembly 118 comprises twenty-two (22) intra-cochlear electrode contacts 126, labeled as electrode contacts 126(1) through 126(22). It is to be appreciated that embodiments presented herein may be implemented in alternative arrangements having different numbers of intra-cochlear electrode contacts.

As shown, the intra-cochlear electrode contacts 126(1)-126(22) are disposed in an elongate carrier member 134. The carrier member 134 has a center longitudinal axis and an outer surface. The carrier member 134 is formed from a non-conductive (insulating) material, such as silicone or other elastomer polymer. As such, the carrier member 134 electrically isolates the intra-cochlear electrode contacts 126(1)-126(22) from one another. As shown in FIG. 1B, the intra-cochlear electrode contacts 126(1)-126(22) are each spaced from one another by sections/segments of the carrier member 134.

The stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1B). Carrier member 134 and lead region 116 each includes a plurality of conductors (wires) extending there through that electrically connect the electrode contacts 126 to the stimulator unit 120.

Also shown in FIG. 1A is an extra-cochlear electrode contact 126(23). The extra-cochlear electrode contact 126(23) is an electrical contact that is configured to, for example, deliver electrical stimulation to the recipient's cochlea and/or to sink current from the recipient's cochlea. The extra-cochlear electrode contact 126(23) is connected to a reference lead 123 that includes one or more conductors that electrically couple the extra-cochlear electrode contact 126(23) to the stimulator unit 120.

As noted above, the closely-coupled wireless link 127 formed between the external coil 106 and the implantable coil 122 may be used to transfer power and/or data from the external component 102 to the implantable component 104. In certain examples, the power and data are transmitted using a type of time division multiple access (TDMA) technique to share the closely-coupled wireless link 127. That is, the closely-coupled wireless link 127 is used to separately transfer power and data from the external component 102 to the implantable component 104, where the transfer of power and data occur during separate (different and non-overlapping) time slots using the same external coil 106 (i.e., a shared external coil for both data and power). For example, during a set of first time periods, the power drive circuitry 146 of the external RF interface circuitry 121 is configured to drive (energize) the external coil 106 in a manner that sends data to the implantable component 104. During a second set of time periods, the data drive circuitry 144 of the external RF interface circuitry 121 is configured to drive (energize) the external coil 106 in a manner that sends power to the implantable component 104. A single transmission sequence/frame may be split into a power time slot (block) and a data time slot (block) and repeated. All of the power towards the implantable component 104 is transferred during the power time slot.

In the example of FIGS. 1A and 1B, the external coil 106 is part of an external resonant circuit (e.g., external resonant tank circuit) 140. Similarly, the implantable coil 122 and at least a portion of the internal RF interface circuitry 124 form an implantable resonant circuit (e.g., internal resonant tank circuit) 142. The external resonant tank circuit 140 and the internal resonant tank circuit 142 collectively form a resonant system 150 which function as the bidirectional closely-coupled wireless link 127.

One measure of the operation of the closely-coupled wireless link 127 (i.e., of the resonant system 150 formed by the external resonant tank circuit 140 and the internal resonant tank circuit 142) is the quality factor (Q) of the link. In general, the quality factor is a ratio of power stored to power dissipated in the resonant system reactance and resistance, respectively. The quality factor is a dimensionless number that describes the damping in the resonant system, as well as provides an indication of the bandwidth relative to the center frequency. A higher value corresponds to a narrower bandwidth.

Returning to FIGS. 1A and 1B, in order to efficiently transfer power from the external component to 102 to the implantable component 104, the closely-coupled wireless link 127 (resonant system 150) should have a high quality factor. That is, the quality factor of the closely-coupled wireless link 127 should be maximized during power transmission, thereby ensuring low power loss. However, as noted, a high quality factor is associated with a narrow bandwidth, which is problematic for transmission of data over the closely-coupled wireless link 127. Therefore, power transmission and data transmission have competing quality factor requirements (i.e., efficient power transmission requires a high/maximum quality factor, while higher bandwidth data requires a lower quality factor).

The techniques presented herein address these competing quality factor requirements for power and data transmissions through the use of different transmit (drive) frequencies at the external resonant circuit 140. More specifically, in the embodiments of FIGS. 1A and 1B, the power drive circuitry 146 is configured to drive the external coil 106 (external resonant inductive coil) at a first frequency to transmit power over the closely-coupled wireless link 127. Both the external resonant circuit 140 and the implantable resonant circuit 142 are substantially tuned to this same first frequency. That is, the external resonant circuit 140 and the implantable resonant circuit 142 are each structurally configured so as to resonate a frequency that is substantially the same as the first frequency. Accordingly, the resonant system 150 may be referred to as being tuned to the first frequency. In other words, in these embodiments, the first frequency for power transmission is the resonant frequency of the resonant system 150 (i.e., the resonant frequency of each of the external resonant circuit 140 and the implantable resonant circuit 142).

Due to the fact that the power transmissions occur at a frequency that substantially matches the tuned frequency of each of the external resonant circuit 140 and the implantable resonant circuit 142 (i.e., the tuned frequency of the resonant system 150), maximum power coupling is achieved with the power transmissions at the first frequency. Stated differently, the matching of the drive/transmit frequency to the tuned frequency of the resonant system 150 provides a high quality factor where, as noted, the higher the quality factor of the system, the more efficient the power transfer will be across the closely-coupled wireless link 127.

While, as noted above, a high quality factor is appropriate for power transmission, a high quality factor reduces the rate that data can be transmitted through the inductive coupling of the closely-coupled wireless link 127 (i.e., reduces the available bandwidth of the closely-coupled wireless link 127). While the quality factor of the resonant system is high when the transmit frequency is at or near the resonant frequency, the quality factor is lower at different frequencies that have an appropriate distance/spacing, in frequency, from the resonant frequency (where the frequency difference is dependent on the shape of the resonance and is selected to provide an appropriate bandwidth for the desired data rate).

Accordingly, an appropriate quality factor for transmitting data can be obtained at transmit frequencies that are spaced some frequency distance from the resonant frequency of the resonant system 150. Therefore, in accordance with embodiments presented herein, data drive circuitry 144 is configured to drive the external resonant circuit 140, including external coil 106, at a second frequency to transmit data over the closely-coupled wireless link 127, where the second frequency is different from the first frequency. During the data transmission, the external resonant circuit 140 and the implantable resonant circuit 142 both remain tuned to the first frequency (i.e., the external resonant circuit 140 and the implantable resonant circuit 142 each have a fixed structure that fixes the tuned frequency thereof). As such, the frequency "mismatch" or difference between the transmit frequency and the frequency of the resonant system 150 causes a reduction in the quality factor of the combined resonant system (i.e., reduces the quality factor of the closely-coupled wireless link 127), which in turn increases the bandwidth available for the transmission of the data.

In summary, FIGS. 1A and 1B illustrate an arrangement in accordance with embodiments presented herein in which, during a first set of time periods, the external resonant circuit 140, which includes external coil 106, is driven at a first frequency to transmit power to the implantable resonant circuit 142, including implantable coil 122. During a second set of time periods, the external resonant circuit 140 is driven at a second frequency to transmit data to the implantable resonant circuit 142, where the second frequency is frequency spaced a frequency distance from the first frequency. During both the first and second sets of time periods, the external resonant circuit 140 and the implantable resonant circuit 142 remain tuned to the first frequency (i.e., the external resonant circuit 140 and the implantable resonant circuit 142 have a fixed tuning).

Figure 2:
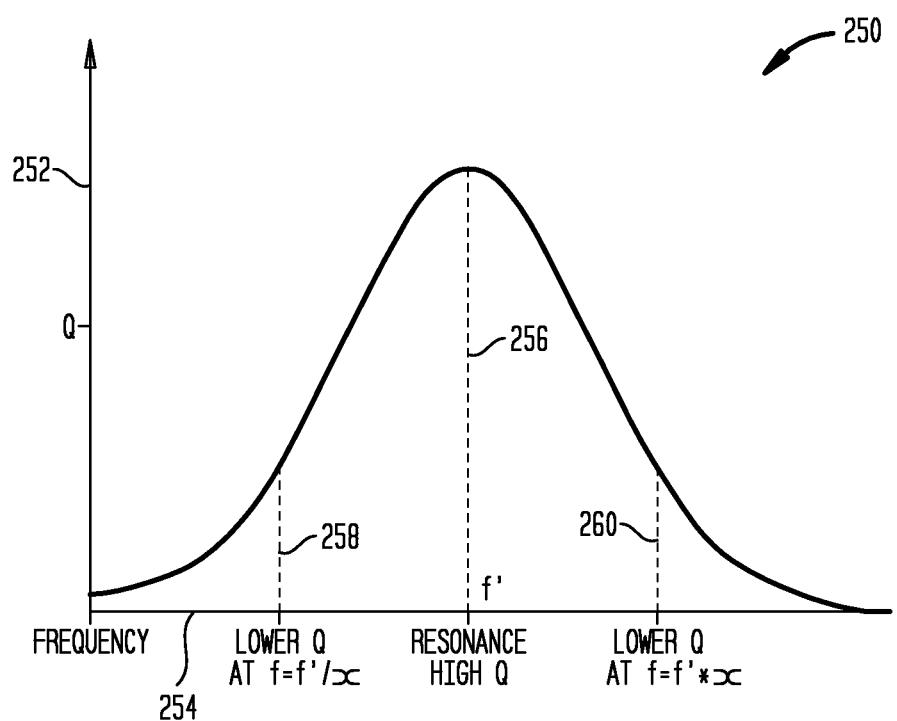
FIG. 2 is a graph illustrating the relationship between the quality factor and operational frequency of a closely-coupled wireless link, in accordance with certain embodiments presented herein.

FIG. 2 is a graph 250 illustrating the relationship between the quality factor and frequency of a bidirectional closely-coupled wireless link, such as closely-coupled wireless link 127. In particular, graph 250 includes a vertical (Y) axis 252 illustrating the quality factor of a closely-coupled wireless link, and a horizontal (X) axis 254 representing the transmit frequency of the closely-coupled wireless link. As represented by line 256, the quality factor is maximized (i.e., is the highest) when the transmit frequency ($f$) (e.g., the frequency at which signals are transmitted by an external coil) is substantially the same as the resonant frequency ($f''$) of the closely-coupled wireless link. As shown by line 258, the quality factor is reduced when the transmit frequency ($f$) is lower than the resonant frequency ($f''$) of the closely-coupled wireless link (e.g., the Q is lower when $f=f''/2$). Similarly, as shown by line 260, the quality factor is also reduced when the transmit frequency ($f$) is higher than the resonant frequency ($f''$) of the closely-coupled wireless link (e.g., the Q is lower when $f=f''*2$).

FIG. 3 is schematic diagram illustrating a resonant system 350 for use in the transcutaneous transfer of power and data, in accordance with embodiments presented herein. As shown, the resonant system 350 includes an external resonant circuit 340 comprising, among other elements, an external coil 306. The resonant system 350 also includes an implantable resonant circuit 342 comprising, among other elements, an internal coil 322. Electrically coupled to, and potentially forming part of, the implantable resonant circuit 342 is internal RF interface circuitry 324, only a portion of which is shown in FIG. 3. The resonant system 350 functions as a closely-coupled wireless link, generally illustrated by arrow 327.

Electrically coupled to the external resonant circuit 340 is external RF interface circuitry 321, only a portion of which is shown in FIG. 3. The external RF interface circuitry 321 comprises, among other elements, data drive circuitry 344, power drive circuitry 346, and a controller 348. The data drive circuitry 344 and power drive circuitry 346 may be selectively activated/used, for example under the control of controller 348, for transcutaneous data and power transmissions via external resonant circuit 340.

More specifically as noted above, in certain examples power and data are transmitted using a type of time division multiple access (TDMA) technique to share the bidirectional closely-coupled wireless link 327 formed by resonant system 350 (i.e., the closely-coupled wireless link 327 is used to separately transfer power and data from the external component 102 to the implantable component 104, where the transfer of power and data occur during separate time slots using the same external coil 306). Therefore, during a set of first time periods, the power drive circuitry 346 is configured to drive (energize) the external coil 306 with power drive signals 364. The power drive signals 364 comprise an alternating waveform having a steady base frequency of alternation (i.e., a constant burst of square wave at the frequency of resonance of the coil). The frequency of alternation of the power drive signals 364 is sometimes referred to herein as the "power transmission frequency" or the "first frequency." The first frequency of the power drive signals 364 corresponds to a resonant frequency of the resonant system 350. That is, the first frequency may be substantially the same as the resonant frequency of the resonant system 350.

When the coil 306 is driven with the power drive signals 364, current flow is induced in the implantable coil 322, where the current flow corresponds to (i.e., represents) the power drive signals 364. As such, via the inductive link between coils 306 and 322, the power drive signals 364 are received at the internal RF interface circuitry 324. The internal RF interface circuitry 324 is configured to direct the power drive signals 364 to, for example, an implantable rechargeable battery and/or other components. For ease of illustration, the various components configured to receive the power drive signals 364 are collectively and generally represented in FIG. 3 by load 363.

During a second set of time periods, the data drive circuitry 344 is configured to drive (energize) the external coil 306 with data drive signals 362 in a manner that sends data to the implantable component. The data drive signals 362 comprise the data to be transmitted (e.g., stimulation control data) that is encoded (modulated) onto a carrier signal (i.e., an alternating waveform having a steady base frequency of alternation), where the carrier signal has a second frequency. The frequency of the data carrier signals (i.e., the frequency of the data drive signals 362) is frequency spaced from the resonant frequency of the resonant system 350, and is sometimes referred to herein as the "data transmission frequency" or the "second frequency."

The data transmission frequency of the data drive signals 362 is frequency spaced a sufficient distance from the resonant frequency of the link 327 to provide the appropriate quality factor for high bandwidth frequency. The data transmission frequency can be higher or lower than the resonant frequency. In certain embodiments, the data transmission frequency may be a multiple or a division of the resonant frequency.

When the coil 306 is driven with the data drive signals 362, current flow is induced in the implantable coil 322, where the current flow corresponds to (i.e., represents) the data drive signals 362. As such, via the inductive link between coils 306 and 322, the data drive signals 362 are received at the internal RF interface circuitry 324. The internal RF interface circuitry 324 is configured to direct the data drive signals 362 to a data output 365 to which any of a number of other components, which have been omitted from FIG. 3 for ease of illustration, may be connected.

As shown, the data drive circuitry 344 and the power drive circuitry 346 are connected to the external resonant circuit 340 via a driver circuit 368, of which a number of different arrangements is possible. In the example of FIG. 3, the driver circuit 368 comprises a switch 372 and an amplifier 374. However, it is to be appreciated that the arrangement for driver circuit 368 shown in FIG. 3 is merely illustrative and that a driver circuit in accordance with embodiments presented herein may have any of a number of different arrangements.

In FIG. 3, the data drive signals 362 and the power drive signals 364 comprise two inputs to the driver circuit 368. The switch 372 operates under the control of controller 348 (i.e., control signal 370) to selectively enable the data drive signals 362 or the power drive signals 364 to pass to the amplifier 374.

In summary, FIG. 3 illustrates an arrangement in which the external resonant circuit 340 is tuned to a frequency used to transmit power signals, and in which the implantable resonant circuit 342 is tuned to the same frequency for maximum power coupling. In this example, the tuned frequency of the external resonant circuit 340 and the tuned frequency of the implantable resonant circuit 342 are each fixed during transmission of both the power (i.e., when driving the coil 306 with the power drive signals 364) and the data (i.e., when driving the coil 306 with the data drive signals 362) (i.e., a fixed resonance for both transmitter and receiver of the link). Accordingly, in accordance with the techniques presented herein, there is no switching of components into or out of either the external resonant circuit 340 or the implantable resonant circuit 342 to change the tuned frequencies or Q factors of the circuits, thereby reducing complexity of the internal and/or external resonant circuitry Although the tuned frequencies of the external resonant circuit 340 and the implantable resonant circuit 342 are fixed, the frequency of transmission of the power and data signals is switched, where the power phase is transmitted at the resonant frequency of the link. The data phase is transmitted at a frequency different from the resonant frequency, far enough from the resonant frequency to provide the appropriate Q for high bandwidth frequency. The data frequency can be higher or lower than the resonant frequency, and the resonant frequency can be any frequency, but may be chosen as the as one of the ISM (Industrial, Scientific and Medical) frequency bands where higher electromagnetic (EM) emissions are allowed.

In the example of FIG. 3, the external resonant circuit 340 and the implantable resonant circuit 342 are "pre-tuned" to the fixed power transmission frequency by design, during manufacture, etc. It is to be noted that the tuning of a coupled system of inductive coils is different from when the coils when uncoupled. Therefore, as used herein, reference to the first frequency (power transmission frequency) or resonant frequency is the frequency that achieves the best power transfer when the external resonant circuit 340 and the implantable resonant circuit 342 are coupled with one another.

Figure 4A:
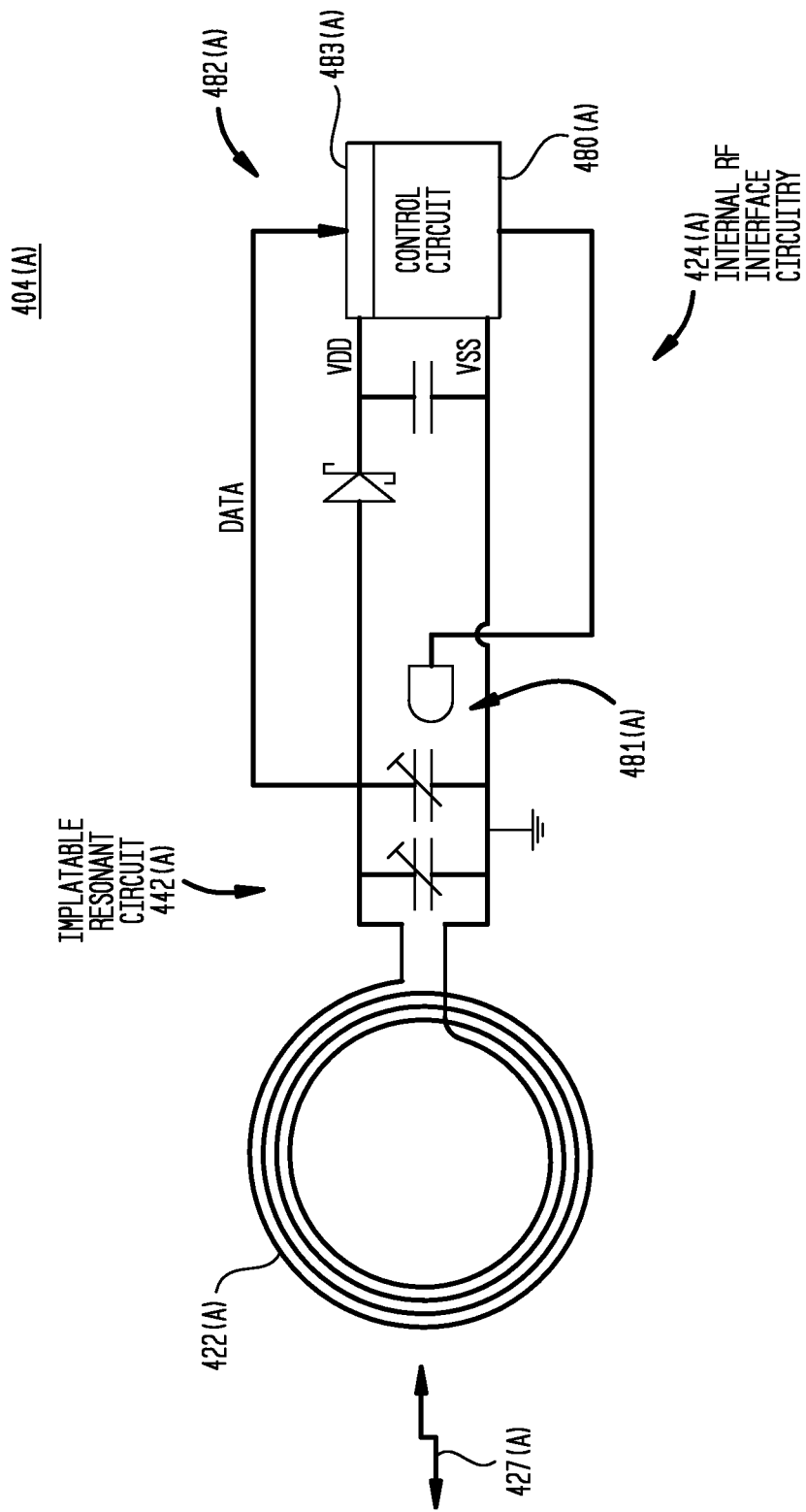
FIG. 4A is a schematic diagram illustrating portion of an implantable component, in accordance with certain embodiments presented herein.

While in the embodiment of FIG. 3 the frequencies of the external resonant circuit 340 and the implantable resonant circuit 342 are fixed and pre-tuned (e.g., by design, during manufacture, etc.), FIG. 4A is a schematic diagram illustrating an alternative embodiment in which at least one of an external resonant circuit or an implantable resonant circuit is self-tuning to the power transmission frequency.

More specifically, shown in FIG. 4A is a portion of an implantable component 404(A), including an implantable resonant circuit 442(A) and internal RF interface circuitry 424(A). The implantable resonant circuit 442(A) includes, among other elements, an implantable coil 422(A). The implantable resonant circuit 442(A) is configured to form a resonant system with an external resonant circuit (not shown in FIG. 4A). The resonant system provides a closely-coupled wireless link 427(A) over which power and data may be sent by an external component (also not shown in FIG. 4A) to the implantable component 404(A). The external resonant circuit may have an arrangement that is similar to the arrangement shown in FIG. 3.

As noted above, resonant systems in accordance with embodiments presented herein that provide a closely-coupled wireless link, such as link 427(A), are designed to be tuned to maximum power coupling. That is, in accordance with embodiments presented herein, during operation, each of the external resonant circuit and the implantable resonant circuit 442(A) are configured to be tuned to substantially the same first frequency, where the first frequency provides a high quality factor. Power signals are then transmitted over the closely-coupled wireless link 427(A) at this same first frequency.

Whereas in FIG. 3 the external resonant circuit and the implantable resonant circuit are pre-tuned to the substantially same first frequency, in the arrangement of FIG. 4A the implantable component 404(A) is configured to dynamically tune the implantable resonant circuit 442(A) to the first frequency. That is, in the example of FIG. 4A, the external resonant circuit has a pre-tuned frequency. Once the implantable resonant circuit 442(A) is coupled to the external resonant circuit (i.e., so as to form the resonant system), the implantable component 404(A) can determine an appropriate tuning for the implantable resonant circuit 442(A).

In the example of FIG. 4A, the implantable component 404(A) includes a control circuit 480(A) that is able to adjust the frequency of resonance (i.e., the tuned frequency) of the implantable resonant circuit 442(A). For example, in the arrangement of FIG. 4A, the implantable resonant circuit 442(A) includes, among other elements, one or more variable capacitance components 481(A) collectively having a capacitance that is controlled/set by the control circuit 480(A). The capacitance of the one or more variable capacitance components 481(A) can be adjusted, for example, in an analog manner, with digital chips designed to switch different capacitors into the circuit, or in another manner. By adjusting the capacitance of the one or more variable capacitance components 481(A) the control circuit 480(A) can adjust the resonant (tuned) frequency of the implantable resonant circuit 442(A) either up or down. Using the power and/or data signals 482(A) received at the implantable resonant circuit 442(A), the control circuit 480(A) can determine the point of maximum power coupling, and accordingly the resonant frequency of the implantable resonant circuit 442(A) at that time. The control circuit 480(A) can then set (i.e., fix) the implantable resonant circuit 442(A) to the correct tuned frequency (i.e., fix the capacitance of the one or more variable capacitance components 481(A) to a level that achieves the selected tuned frequency for implantable resonant circuit 442(A)). These examples may be advantageous in that, during manufacturing of the system, there will be no "set tuning" stage for at least the implantable resonant circuit 442(A).

As noted above, in the example of FIG. 4A, the control circuit 480(A) is configured determine the tuned frequency of the implantable resonant circuit 442(A) that provides a maximum power coupling with the external resonant circuit (i.e., when the implantable resonant circuit 442(A) is tuned to a frequency that substantially matches the tuned frequency of the external resonant circuit). In certain examples, the control circuit 480(A) includes or is coupled to a measurement circuit 483(A) that can be used to measure the voltage of the received signals 482(A) or to use the received signals 482(A) to determine the power being drawn over the RF link (e.g., switching a resistor and measuring the rectified voltage enables determination of the amount of power drawn). In certain embodiments, the control circuit 480(A) may adjust the capacitance of the one or more variable capacitance components 481(A) to increase or decrease the tuned frequency of the implantable resonant circuit 442(A) in a manner that increases the power measured at the measurement circuit 483(A). The control circuit 480(A) continues this adjustment until a decrease in the power measured at the measurement circuit 483(A) is detected, at which point the control circuit 480(A) reverses the adjustment to again increase the power. Using increasingly smaller up and down adjustments to the tuned frequency (i.e., to the capacitance of the one or more variable capacitance components 481(A)), the control circuit 480(A) can accurately lock to the correct tuned frequency (e.g., to a substantially same frequency as that of the external resonant circuit). Once this dynamic tuning is completed, the implantable resonant circuit 442 remains tuned to the tuned frequency (e.g., the same first) during receipt of both power and data from the external component.

FIG. 4A illustrates an example in which the control circuit 480(A) determines the tuned frequency for the implantable resonant circuit 442(A) by determining the point of maximum power coupling. In an alternative embodiment, the control circuit 480(A) could directly measure the frequency of the received signals 482(A) (i.e., identify the pre-tuned frequency of the external resonant circuit) and then adjust the capacitance of the one or more variable capacitance components 481(A) of the implantable resonant circuit 442 based thereon (e.g., so that the implantable resonant circuit 442 is tuned to the substantially same first frequency).

As noted, in the example of FIG. 4A, the control circuit 480(A) is configured to determine the point of maximum power coupling for the resonant system formed by the implantable resonant circuit 442(A) and an external resonant circuit, and accordingly the resonant frequency of the implantable resonant circuit 442(A) at that time. In an alternative arrangement, the control circuit 480(A) could adjust the frequency, not to maximum power coupling, but to a non-optimized power coupling. As used herein, a non-optimized power coupling is power coupling that is lower the maximum power coupling, but which is suitable to power the implantable component and/or is suitable to protect against the receipt of too much power. For example, the use of a non-optimized power coupling could prevent damage to the internal component 404(A) when an external component sends and there is no feedback to the external component (i.e., de-tuning the implantable resonant circuit 442(A) results in greater power loss across the link, meaning there is less power received).

As noted, in the example of FIG. 4A, the control circuit 480(A) adjusts the capacitance of the one or more variable capacitance components 481(A) to adjust/change the resonant (tuned) frequency of the implantable resonant circuit 442(A). It is to be appreciated that this technique for adjusting the resonant frequency of the internal resonant is merely illustrative and that the resonant frequency of an implantable resonant circuit may be changed in other manners.

For example, FIG. 4B is a schematic diagram of a portion of an implantable component 404(B), including an implantable resonant circuit 442(B) and internal RF interface circuitry 424(B). The implantable resonant circuit 442(B) includes, among other elements, an implantable coil 422(A). The implantable resonant circuit 442(B) is configured to form a resonant system with an external resonant circuit (not shown in FIG. 4B). The resonant system provides a closely-coupled wireless link 427(B) over which power and data may be sent by an external component (also not shown in FIG. 4B) to the implantable component 404(B). The external resonant circuit may have an arrangement that is similar to the arrangement shown in FIG. 3.

As noted above, resonant systems in accordance with embodiments presented herein that provide a closely-coupled wireless link, such as link 427(B), are designed to be tuned to maximum power coupling. That is, in accordance with embodiments presented herein, during operation, each of the external resonant circuit and the implantable resonant circuit 442(B) are configured to be tuned to substantially the same first frequency, where the first frequency provides a high quality factor. Power signals are then transmitted over the closely-coupled wireless link 427(B) at this same first frequency.

Whereas in FIG. 3 the external resonant circuit and the implantable resonant circuit are pre-tuned to the substantially same first frequency, in the arrangement of FIG. 4B the implantable component 404(B) is configured to dynamically tune the implantable resonant circuit 442(B) to the first frequency. That is, in the example of FIG. 4B, the external resonant circuit has a pre-tuned frequency. Once the implantable resonant circuit 442(B) is coupled to the external resonant circuit (i.e., so as to form the resonant system), the implantable component 404(B) can determine an appropriate tuning for the implantable resonant circuit 442(B).

In the example of FIG. 4B, the implantable component 404(B) includes a control circuit 480(B) that is able to adjust the frequency of resonance (i.e., the tuned frequency) of the implantable resonant circuit 442(B). For example, in the arrangement of FIG. 4B, the implantable resonant circuit 442(B) includes, among other elements, one or more variable inductance components 485(B) collectively having an inductance that is controlled/set by the control circuit 480(B). The inductance of the one or more variable inductance components 485(B) can be adjusted, for example, in an analog manner, with digital chips designed to switch different inductors into the circuit, or in another manner. By adjusting the inductance of the one or more variable inductance components 485(B) the control circuit 480(B) can adjust the resonant (tuned) frequency of the implantable resonant circuit 442(B) either up or down. Using the power and/or data signals 482(B) received at the implantable resonant circuit 442(B), the control circuit 480(B) can determine the point of maximum power coupling, and accordingly the resonant frequency of the implantable resonant circuit 442(B) at that time. The control circuit 480(B) can then set (i.e., fix) the implantable resonant circuit 442(B) to the correct tuned frequency (i.e., fix the capacitance of the one or more variable inductance components 485(B) to a level that achieves the selected tuned frequency for implantable resonant circuit 442(B)). These examples may be advantageous in that, during manufacturing of the system, there will be no "set tuning" stage for at least the implantable resonant circuit 442(B).

As noted above, in the example of FIG. 4B, the control circuit 480(B) is configured determine the tuned frequency of the implantable resonant circuit 442(B) that provides a maximum power coupling with the external resonant circuit (i.e., when the implantable resonant circuit 442(B) is tuned to a frequency that substantially matches the tuned frequency of the external resonant circuit). In certain examples, the control circuit 480(B) includes or is coupled to a measurement circuit 483(B) that can be used to measure the voltage of the received signals 482(B) or to use the received signals 482(B) to determine the power being drawn over the RF link (e.g., switching a resistor and measuring the rectified voltage enables determination of the amount of power drawn). In certain embodiments, the control circuit 480(B) may adjust the inductance of the one or more variable inductance components 485(B) to increase or decrease the tuned frequency of the implantable resonant circuit 442(B) in a manner that increases the power measured at the measurement circuit 483(B). The control circuit 480(B) continues this adjustment until a decrease in the power measured at the measurement circuit 483(B) is detected, at which point the control circuit 480(B) reverses the adjustment to again increase the power. Using increasingly smaller up and down adjustments to the tuned frequency (i.e., to the inductance of the one or more variable inductance components 485(B)), the control circuit 480(B) can accurately lock to the correct tuned frequency (e.g., to a substantially same frequency as that of the external resonant circuit). Once this dynamic tuning is completed, the implantable resonant circuit 442 remains tuned to the tuned frequency (e.g., the same first) during receipt of both power and data from the external component.

FIG. 4A illustrates an example in which the control circuit 480(B) determines the tuned frequency for the implantable resonant circuit 442(B) by determining the point of maximum power coupling. In an alternative embodiment, the control circuit 480(B) could directly measure the frequency of the received signals 482(B) (i.e., identify the pre-tuned frequency of the external resonant circuit) and then adjust the capacitance of the one or more variable inductance components 485(B) of the implantable resonant circuit 442 based thereon (e.g., so that the implantable resonant circuit 442 is tuned to the substantially same first frequency).

As noted, in the example of FIG. 4A, the control circuit 480(A) adjusts the capacitance of the one or more variable capacitance components 481(A) to adjust/change the resonant (tuned) frequency of the implantable resonant circuit 442(A). In FIG. 4B, the control circuit 480(B) adjusts the inductance of the one or more variable inductance components 485(B) to adjust/change the resonant (tuned) frequency of the implantable resonant circuit 442(B). It is to be appreciated that these two techniques for adjusting the resonant frequency of the internal resonant are merely illustrative and that the resonant frequency of an implantable resonant circuit may be changed in other manners.

Figure 4C:
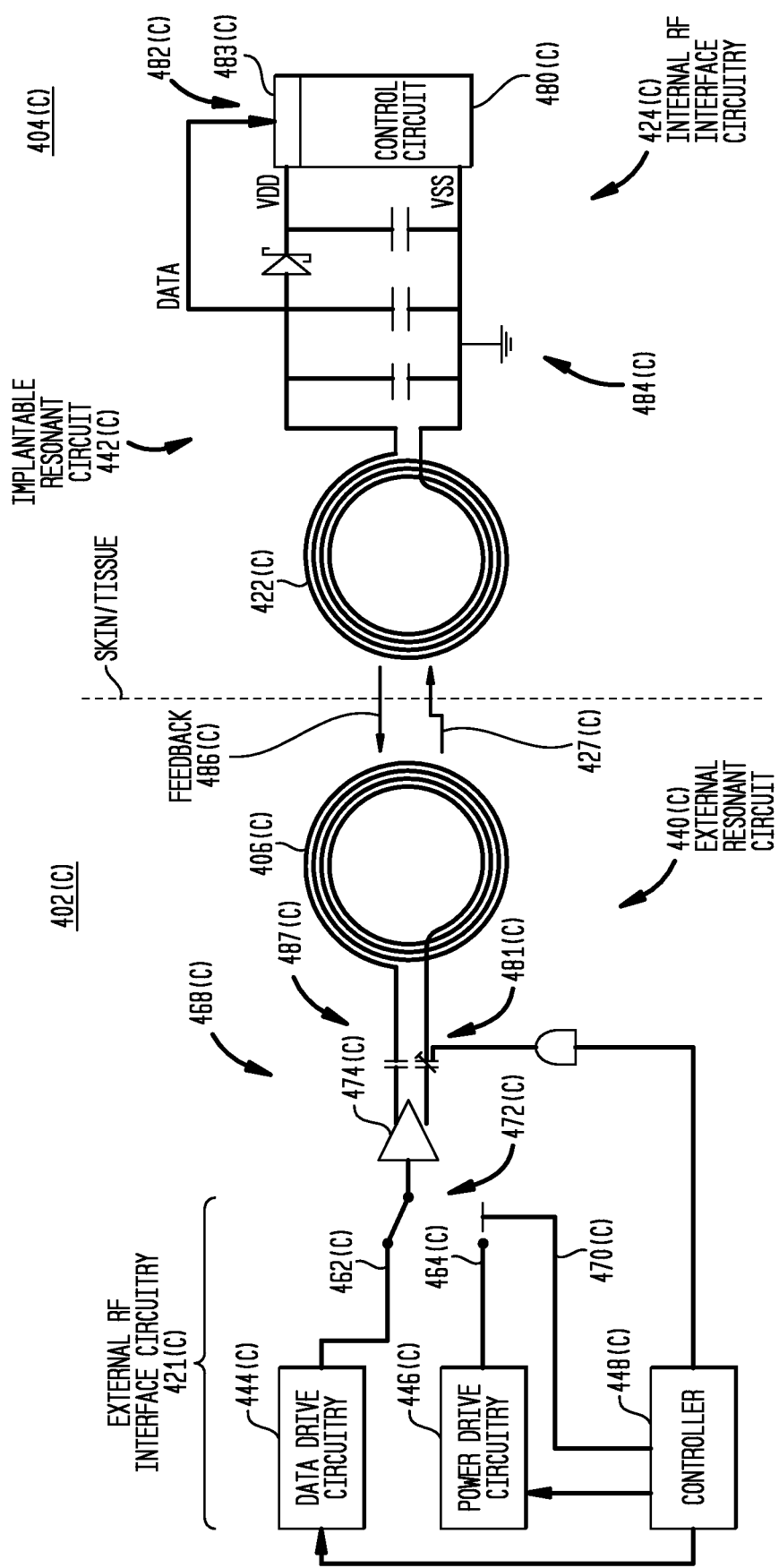
FIG. 4C is a schematic diagram illustrating portions of an external component and an implantable component, in accordance with certain embodiments presented herein.

FIGS. 4A and 4B illustrate embodiments in which the tuned frequencies of implantable resonant circuits are adjusted/tuned to a substantially same frequency as a coupled external resonant circuit. FIG. 4C illustrates an alternative embodiment in which an external resonant circuit can be tuned to match the frequency of an implantable resonant circuit.

More specifically, shown in FIG. 4C is a portion of an external component 402(C) and an implantable component 404(C), in accordance with embodiments presented herein. The external component 402(C) comprises an external resonant circuit 440(C), while the implantable component 404(C) comprises an implantable resonant circuit 442(C). Collectively, the external resonant circuit 440(C) and the implantable resonant circuit 442(C) for a resonant system 450(C) for use in the transcutaneous transfer of power and data, in accordance with embodiments presented herein.

The external resonant circuit 440(C) comprises, among other elements, an external coil 406(C) and capacitive components 487(C), including one or more variable capacitance components 481(C). The implantable resonant circuit 442(C) comprises, among other elements, an internal coil 422(C) and capacitive components 489(C). Electrically coupled to, and potentially forming part of, the implantable resonant circuit 442(C) is internal RF interface circuitry 424(C), only a portion of which is shown in FIG. 4C. The resonant system 450(C) functions as a bidirectional closely-coupled wireless link, generally illustrated by arrow 427(C).

Electrically coupled to the external resonant circuit 440(C) is external RF interface circuitry 421(C), only a portion of which is shown in FIG. 4C. The external RF interface circuitry 421(C) comprises, among other elements, data drive circuitry 444(C), power drive circuitry 446(C), and a controller 448(C). Similar to as described above with reference to FIG. 3, the data drive circuitry 444(C) and power drive circuitry 446(C) may be selectively activated/used, for example under the control of controller 448, for transcutaneous data and power transmissions via external resonant circuit 440(C).

More specifically, as noted above, in certain examples power and data are transmitted using a type of time division multiple access (TDMA) technique to share the closely-coupled wireless link 427(C) formed by resonant system 450(C) (i.e., the closely-coupled wireless link 427(C) is used to separately transfer power and data from the external component 402(C) to the implantable component 404(C), where the transfer of power and data occur during separate time slots using the same external coil 406(C)). Therefore, during a set of first time periods, the power drive circuitry 446(C) is configured to drive (energize) the external coil 406(C) with power drive signals 464(C). The power drive signals 464(C) comprise an alternating waveform having a steady base frequency of alternation (i.e., a constant burst of square wave at the frequency of resonance of the coil). The frequency of alternation of the power drive signals 464(C) is sometimes referred to herein as the "power transmission frequency" or the "first frequency." The first frequency of the power drive signals 464(C) corresponds to a resonant frequency of the resonant system 450(C). That is, the first frequency may be substantially the same as the resonant frequency of the resonant system 450(C).

When the coil 406(C) is driven with the power drive signals 464(C), current flow is induced in the implantable coil 422(C), where the current flow corresponds to (i.e., represents) the power drive signals 464(C). As such, via the inductive link between coils 406(C) and 422(C), the power drive signals 464(C) are received at the internal RF interface circuitry 424(C). The internal RF interface circuitry 424(C) is configured to direct the power drive signals 464(C) to, for example, an implantable rechargeable battery and/or other components.

During a second set of time periods, the data drive circuitry 444(C) is configured to drive (energize) the external coil 406(C) with data drive signals 462(C) in a manner that sends data to the implantable component. The data drive signals 462(C) comprise the data to be transmitted (e.g., stimulation control data) that is encoded (modulated) onto a carrier signal (i.e., an alternating waveform having a steady base frequency of alternation), where the carrier signal has a second frequency. The frequency of the data carrier signals (i.e., the frequency of the data drive signals 462) is frequency spaced from the resonant frequency of the resonant system 450(C), and is sometimes referred to herein as the "data transmission frequency" or the "second frequency."

The data transmission frequency of the data drive signals 462(C) is frequency spaced a sufficient distance from the resonant frequency of the link 427(C) to provide the appropriate quality factor for high bandwidth frequency. The data transmission frequency can be higher or lower than the resonant frequency. In certain embodiments, the data transmission frequency may be a multiple or a division of the resonant frequency.

When the coil 406(C) is driven with the data drive signals 462(C), current flow is induced in the implantable coil 422(C), where the current flow corresponds to (i.e., represents) the data drive signals 462(C). As such, via the inductive link between coils 406(C) and 422(C), the data drive signals 462(C) are received at the internal RF interface circuitry 424(C). The internal RF interface circuitry 424(C) is configured to direct the data drive signals 462(C) to a data output to which any of a number of other components, which have been omitted from FIG. 4C for ease of illustration, may be connected.

As shown, the data drive circuitry 444(C) and the power drive circuitry 446(C) are connected to the external resonant circuit 440(C) via a driver circuit 468(C), of which a number of different arrangements is possible. In the example of FIG. 4C, the driver circuit 468(C) comprises a switch 472(C) and an amplifier 474(C). However, it is to be appreciated that the arrangement for driver circuit 468(C) shown in FIG. 4C is merely illustrative and that a driver circuit in accordance with embodiments presented herein may have any of a number of different arrangements.

In FIG. 4C, the data drive signals 462(C) and the power drive signals 464(C) comprise two inputs to the driver circuit 468(C). The switch 472(C) operates under the control of controller 448(C) (i.e., control signal 470(C)) to selectively enable the data drive signals 462(C) or the power drive signals 464(C) to pass to the amplifier 474(C).

Resonant systems in accordance with embodiments presented herein that provide a closely-coupled wireless link, such as link 427(C), are designed to be tuned to maximum power coupling. That is, in accordance with embodiments presented herein, during operation, each of the external resonant circuit 440(C) and the implantable resonant circuit 442(C) are configured to be tuned to substantially the same first frequency, where the first frequency provides a high quality factor. Power signals are then transmitted over the closely-coupled wireless link 427(C) at this same first frequency.

Whereas in FIG. 3 the external resonant circuit and the implantable resonant circuit are pre-tuned to the substantially same first frequency, in the arrangement of FIG. 4C the external component 402(C) is configured to dynamically tune the external resonant circuit 440(C) to a frequency that matches a tuned frequency of the implantable resonant circuit 442(C). The data drive circuitry 444(C) and the power drive circuitry 446(C) can also be programmed based on the tuned frequency of the implantable resonant circuit 442(C). That is, in the example of FIG. 4C, the implantable resonant circuit 442(C) has a pre-tuned frequency. Once the external resonant circuit 440(C) is coupled to the implantable resonant circuit 442(C) (i.e., so as to form the resonant system 450(C)), the external component 402(C) can determine an appropriate tuning for the external resonant circuit 440(C), as well as appropriate frequencies for the data drive signals 462(C) and/or the power drive signals 464(C).

In the example of FIG. 4C, the implantable component 404(C) includes a control circuit 480(C) that is able to provide feedback 486(C) to the external component 402(C). Using the feedback 486(C), the controller 448(C) of the external component 402(C) can adjust the frequency of resonance (i.e., the tuned frequency) of the external resonant circuit 440(C), as well as appropriate frequencies for the data drive signals 462(C) and/or the power drive signals 464(C). For example, in the arrangement of FIG. 4C, the external resonant circuit 440(C) includes, among other elements, one or more variable capacitance components 481(C) collectively having a capacitance that is controlled/set by the controller 448(C). The capacitance of the one or more variable capacitance components 481(C) can be adjusted, for example, in an analog manner, with digital chips designed to switch different capacitors into the circuit, or in another manner. By adjusting the capacitance of the one or more variable capacitance components 481(C) the control circuit 480(C) can adjust the resonant (tuned) frequency of the external resonant circuit 440(C) either up or down.

The control circuit 480(C) is configured to use the power and/or data signals 482(C) received at the implantable resonant circuit 442(C) to determine the point of maximum power coupling, and accordingly to generate the feedback 486(C). The controller 448(C) can then set (i.e., fix) the external resonant circuit 440(C) to the correct tuned frequency (i.e., fix the capacitance of the one or more variable capacitance components 481(C) to a level that achieves the selected tuned frequency for external resonant circuit 440(C) when the feedback 486(C) indicates a maximum power coupling. These examples may be advantageous in that, during manufacturing of the system, there will be no "set tuning" stage for at least the implantable resonant circuit 442(C).

As noted above, in the example of FIG. 4C, the control circuit 480(C) is configured determine the tuned frequency of the implantable resonant circuit 442(C) that provides a maximum power coupling with the external resonant circuit (i.e., when the implantable resonant circuit 442(C) is tuned to a frequency that substantially matches the tuned frequency of the external resonant circuit). In certain examples, the control circuit 480(C) includes or is coupled to a measurement circuit 483(C) that can be used to measure the voltage of the received signals 482(C) or to use the received signals 482(C) to determine the power being drawn over the RF link (e.g., switching a resistor and measuring the rectified voltage enables determination of the amount of power drawn). In certain embodiments, the control circuit 480(C) may generate the feedback 486(C) so as to cause the controller 448(C) in the external component 402(C) to adjust the capacitance of the one or more variable capacitance components 481(C) in a manner that increases or decreases the tuned frequency of the external resonant circuit 440(C) in a manner that increases the power measured at the measurement circuit 483(C). The control circuit 480(C) continues to generate feedback 486(C) causing such adjustments until a decrease in the power measured at the measurement circuit 483(C) is detected. At this point, the control circuit 480(C) generates feedback 486(C) causing a reversal in the adjustment to again increase the power. Using increasingly smaller up and down adjustments to the tuned frequency (i.e., to the capacitance of the one or more variable capacitance components 481(C)), the controller 448(C) can, using feedback from the control circuit 480(C), accurately lock to the correct tuned frequency (e.g., to a substantially same frequency as that of the implantable resonant circuit). Once this dynamic tuning is completed, the external resonant circuit 440(C) remains tuned to the tuned frequency (e.g., the same first) during receipt of both power and data from the external component.

FIG. 4C illustrates an example in which the tuned frequency for the external resonant circuit 440(C) is determined based on the point of maximum power coupling. Similar to the above embodiments, the tuned frequency for the external resonant circuit 440(C) could alternatively be set based on a measurement the frequency of the received signals 482(C) or in another manner. In a still other alternative arrangement, the control circuit 480(C) and controller 448(C) could operate to adjust the tuned frequency of the external resonant circuit 440(C), not to maximum power coupling, but to a non-optimized power coupling.

As noted, in the example of FIG. 4C, the controller 448(C)) adjusts the capacitance of the one or more variable capacitance components 481(C) to adjust/change the resonant (tuned) frequency of the implantable resonant circuit 442(C). It is to be appreciated that this technique for adjusting the resonant frequency of the internal resonant is merely illustrative and that the resonant frequency of an implantable resonant circuit may be changed in other manners (e.g., adjustable/variable inductance, etc.).

Figure 5:
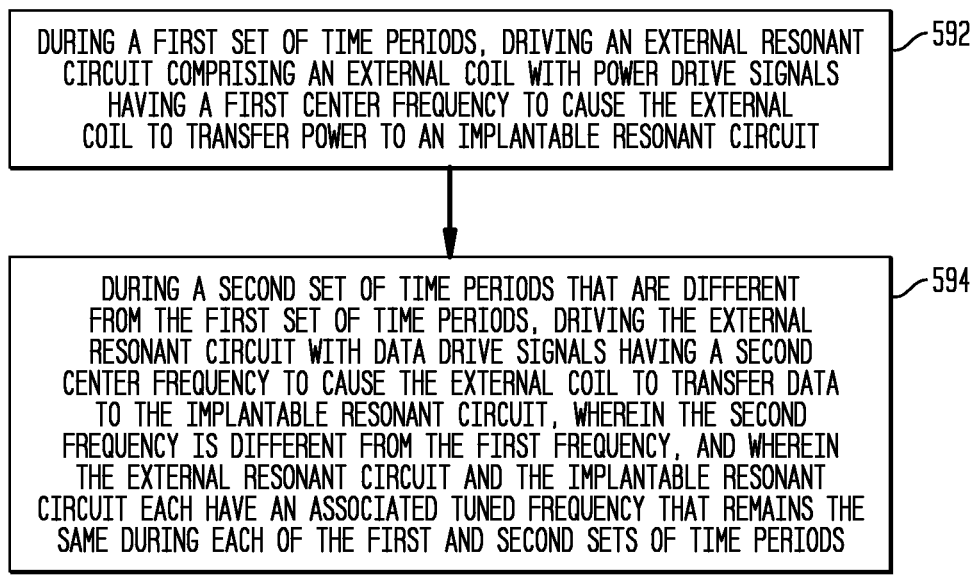
FIG. 5 is flowchart of a method, in accordance with certain embodiments presented herein.

FIG. 5 is a flowchart of a method 590 in accordance with embodiments presented herein. Method 590 begins at 592 where, during a first set of time periods, circuitry drives an external resonant circuit comprising an external coil with power drive signals having a first center frequency to cause the external coil to transfer power to an implantable resonant circuit. At 594, during a second set of time periods that are different from the first set of time periods, the circuitry drives the external resonant circuit with data drive signals having a second center frequency to cause the external coil to transfer data to the implantable resonant circuit. The second frequency is different from the first frequency, and the external resonant circuit and the implantable resonant circuit each have an associated tuned frequency that remains the same during each of the first and second sets of time periods.

FIG. 6 is a flowchart of a method 690 in accordance with embodiments presented herein. Method 690 begins at 592 where an external resonant circuit of an external component of an implantable medical devices sends power signals to an implantable resonant circuit of the implantable medical device, wherein the power signals have a first frequency. At 694, the external resonant circuit sends data signals to the implantable resonant circuit, wherein the data signals have a second frequency. A physical arrangement of each of the implantable resonant circuit and the external resonant circuit does not change whether sending the power or data signals to the implantable resonant circuit.

As noted above, merely for purposes of illustration, the techniques presented herein have been described with reference to a cochlear implant having an external component and an implantable component. However, it is to be appreciated that the techniques presented herein any be implemented in any of a number of different types of implantable medical device systems in which power and data are transferred over a transcutaneous communication link. For example, the techniques presented herein may be used in any other partially or fully implantable medical devices now known or later developed, including other auditory prostheses, such as auditory brainstem stimulators, electro-acoustic hearing prostheses, acoustic hearing aids, bone conduction devices, middle ear prostheses, direct cochlear stimulators, bimodal hearing prostheses, etc. The techniques presented herein may also be used with balance prostheses (e.g., vestibular implants), retinal or other visual prosthesis/stimulators, occipital cortex implants, sensor systems, implantable pacemakers, drug delivery systems, defibrillators, catheters, seizure devices (e.g., devices for monitoring and/or treating epileptic events), sleep apnea devices, electroporation devices, spinal cord stimulators, deep brain stimulators, motor cortex stimulators, sacral nerve stimulators, pudendal nerve stimulators, vagus/vagal nerve stimulators, trigeminal nerve stimulators, diaphragm (phrenic) pacers, pain relief stimulators, other neural, neuromuscular, or functional stimulators, etc.

Figure 7:
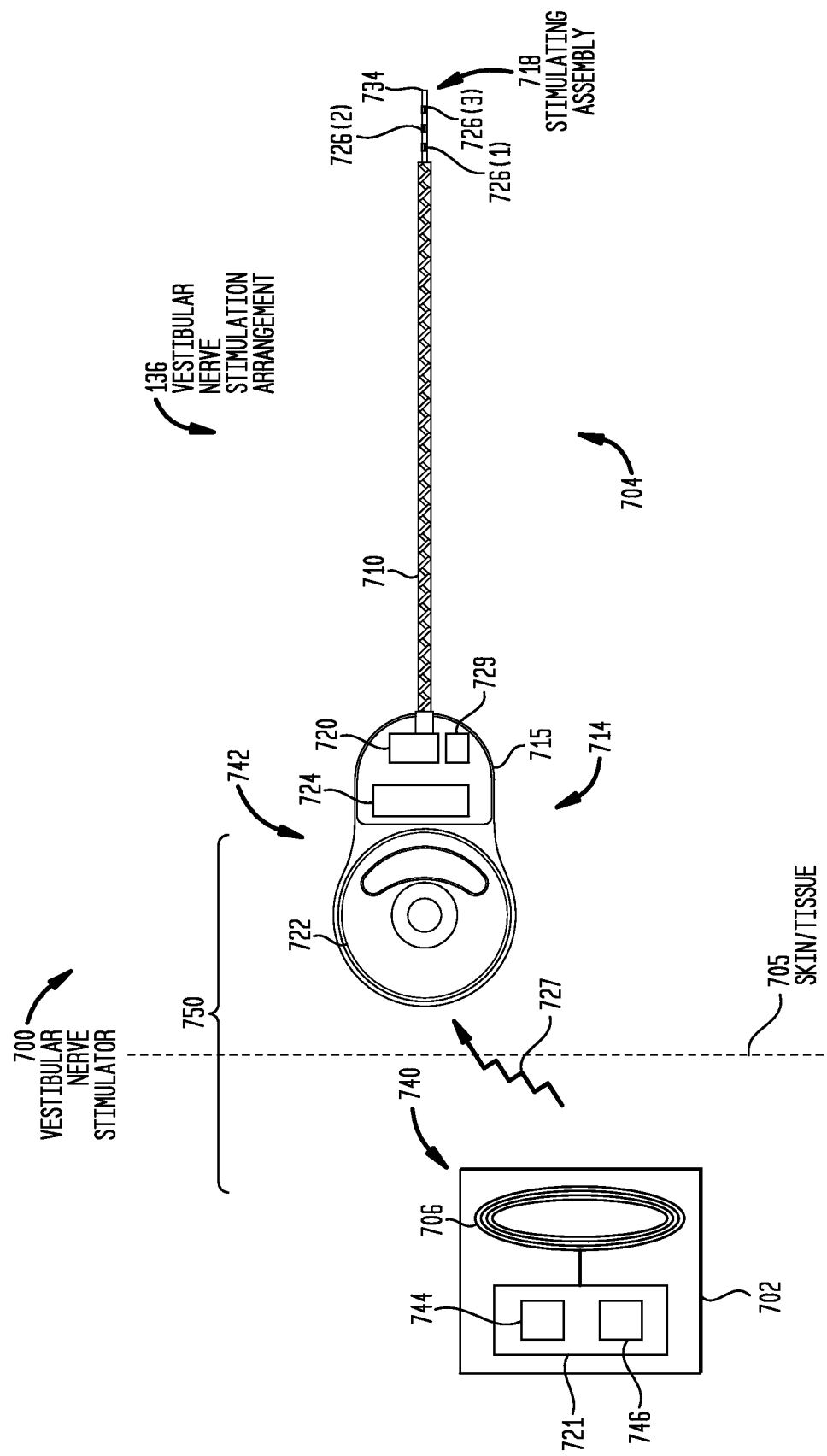
FIG. 7 is a schematic diagram illustrating a balance prosthesis in which the techniques presented herein may be implemented.

FIG. 7 is a schematic diagram illustrating a balance prosthesis in which the techniques presented herein may be implemented. It is to be appreciated is merely illustrative one additional type of implantable medical device in which the techniques presented herein may be implemented.

More specifically, certain individuals may suffer from a balance disorder with complete or partial loss of vestibular system function/sensation in one or both ears. In general, a balance disorder is a condition in which an individual lacks the ability to control and/or maintain a proper (balanced) body position in a comfortable manner (i.e., the recipient experiences some sensation(s) of disbalance). Disbalance, sometimes referred to herein as balance problems, can manifest in a number of different manners, such as feelings of unsteadiness or dizziness, a feeling of movement, spinning, or floating, even though standing still or lying down, falling, difficulty walking in darkness without falling, blurred or unsteady vision, inability to stand or walk unaided, etc. Balance disorders can be caused by certain health conditions, medications, aging, infections, head injuries, problems in the inner ear, problems with brain or the heart, problems with blood circulation, etc. In general, a "balance prosthesis" or "balance implant" is a medical device that is configured to assist recipients (i.e., persons in which a balance prosthesis is implanted) that suffer from balance disorders.

As noted, FIG. 7 illustrates one example balance prosthesis, namely a vestibular nerve stimulator 700, in accordance with embodiments presented herein. More specifically, as shown in FIG. 7, the vestibular nerve stimulator 700 comprises an external component 702 and an implantable component 704, which is implantable within a recipient (i.e., implanted under the skin/tissue 705 of a recipient).

The external component 702 may comprise a number of functional and/or electronic elements used in the operation of the vestibular nerve stimulator 700. However, for ease of understanding, FIG. 7 only illustrates external radio frequency (RF) interface circuitry 721 and an external coil 706. The external coil 706 is part of an external resonant circuit 740. As described further below, the external RF interface circuitry 721 comprises data drive circuitry 744 and power drive circuitry 746 which are selectively activated/used for transcutaneous transmissions of data and power, respectively, to the implantable component 704.

The implantable component 704 comprises an implant body (main module) 714 and a vestibular stimulation arrangement 737. The implant body 734 generally comprises a hermetically-sealed housing 715 in which a number of functional and/or electronic elements used in the operation of the vestibular nerve stimulator 700 may be disposed. However, for ease of understanding, FIG. 7 only illustrates internal radio frequency (RF) interface circuitry 724, a stimulator unit 720, and a rechargeable battery 729. The implant body 734 also includes an internal/implantable coil 722 that is generally external to the housing 715, but which is connected to the internal RF interface circuitry 724 via a hermetic feedthrough (not shown in FIG. 7). The implantable coil 722 is part of an implantable resonant circuit 742. The stimulator unit 720 may include, for example, one or more current sources, switches, etc., that collectively operate to generate and deliver the electrical stimulation signals to the recipient via the vestibular stimulation arrangement 737.

As shown in FIG. 7, the vestibular stimulation arrangement 737 comprises a lead 716 and a vestibular nerve stimulating (electrode) assembly 718. The stimulating assembly 718 comprises a plurality of electrodes 726 disposed in a carrier member 734 (e.g., a flexible silicone body). In this specific example, the stimulating assembly 718 comprises three (3) electrodes, referred to as electrodes 726(1), 726(2), and 726(3). The electrodes 726(1), 726(2), and 726(3) function as an electrical interface to the recipient's vestibular nerve. It is to be appreciated that this specific embodiment with three electrodes is merely illustrative and that the techniques presented herein may be used with stimulating assemblies having different numbers of electrodes, stimulating assemblies having different lengths, etc.

The stimulating assembly 718 is configured such that a surgeon can implant the stimulating assembly adjacent the otolith organs of the peripheral vestibular system via, for example, the recipient's oval window. That is, the stimulating assembly 718 has sufficient stiffness and dynamics such that the stimulating assembly can be inserted through the oval window and placed reliably within the bony labyrinth adjacent the otolith organs (e.g., sufficient stiffness to insert the stimulating assembly to the desired depth between the bony labyrinth and the membranous labyrinth).

As noted above, the external component 702 comprises an external resonant circuit 740, which includes the external coil 706. Similarly, the implantable component 704 comprises an implantable resonant circuit 742, which includes the implantable coil 722. When the coils 706 and 722 are positioned in close proximity to one another, the coils form a transcutaneous closely-coupled wireless link 727. This closely-coupled wireless link 727 formed between the external coil 706 with the implantable coil 722 may be used to transfer power and/or data from the external component 702 to the implantable component 704. In certain examples, the power and data are transmitted using a type of time division multiple access (TDMA) technique to share the closely-coupled wireless link 727. That is, the closely-coupled wireless link 727 is used to separately transfer power and data from the external component 702 to the implantable component 704, where the transfer of power and data occur during separate (different and non-overlapping) time slots using the same external coil 706 (i.e., a shared external coil for both data and power). For example, during a set of first time periods, the power drive circuitry 746 of the external RF interface circuitry 721 is configured to drive (energize) the external coil 706 in a manner that sends data to the implantable component 104. During a second set of time periods, the data drive circuitry 744 of the external RF interface circuitry 721 is configured to drive (energize) the external coil 706 in a manner that sends power to the implantable component 704.

As noted, in the example of FIG. 7, the external coil 706 is part of an external resonant circuit (e.g., external resonant tank circuit) 740. Similarly, the implantable coil 722 and at least a portion of the internal RF interface circuitry 724 form an implantable resonant circuit (e.g., internal resonant tank circuit) 742. The external resonant tank circuit 740 and the internal resonant tank circuit 742 collectively form a resonant system 750 which function as closely-coupled wireless link 727.

In order to efficiently transfer power from the external component to 702 to the implantable component 704, the closely-coupled wireless link 727 (resonant system 750) should have a high quality factor. That is, the quality factor of the closely-coupled wireless link 727 should be maximized during power transmission, thereby ensuring low power loss. However, as noted, a high quality factor is associated with a narrow bandwidth, which is problematic for transmission of data over the closely-coupled wireless link 727. Therefore, power transmission and data transmission have competing quality factor requirements (i.e., efficient power transmission requires a high/maximum quality factor, while higher bandwidth data requires a lower quality factor).

The techniques presented herein address these competing quality factor requirements for power and data transmissions through the use of different transmit (drive) frequencies at the external resonant circuit 740. More specifically, in the embodiments of FIG. 7, the power drive circuitry 746 is configured to drive the external coil 706 (external resonant inductive coil) at a first frequency to transmit power over the closely-coupled wireless link 727. Both the external resonant circuit 740 and the implantable resonant circuit 742 are substantially tuned to this same first frequency. That is, the external resonant circuit 740 and the implantable resonant circuit 742 are each structurally configured so as to resonate a frequency that is substantially the same as the first frequency. Accordingly, the resonant system 750 may be referred to as being tuned to the first frequency. In other words, in these embodiments, the first frequency for power transmission is the resonant frequency of the resonant system 750 (i.e., the resonant frequency of each of the external resonant circuit 740 and the implantable resonant circuit 742).

Due to the fact that the power transmissions occur at a frequency that substantially matches the tuned frequency of each of the external resonant circuit 740 and the implantable resonant circuit 742 (i.e., the tuned frequency of the resonant system 750), maximum power coupling is achieved with the power transmissions at the first frequency. Stated differently, the matching of the drive/transmit frequency to the tuned frequency of the resonant system 750 provides a high quality factor where, as noted, the higher the quality factor of the system, the more efficient the power transfer will be across the closely-coupled wireless link 727.

While, as noted above, a high quality factor is appropriate for power transmission, a high quality factor reduces the rate that data can be transmitted through the inductive coupling of the closely-coupled wireless link 727 (i.e., reduces the available bandwidth of the closely-coupled wireless link 727). While the quality factor of the resonant system is high when the transmit frequency is at or near the resonant frequency, the quality factor is lower at different frequencies that have an appropriate distance/spacing, in frequency, from the resonant frequency. Accordingly, an appropriate quality factor for transmitting data can be obtained at transmit frequencies that are spaced some frequency distance from the resonant frequency of the resonant system 750. Therefore, in accordance with embodiments presented herein, data drive circuitry 744 is configured to drive the external resonant circuit 740, including external coil 706, at a second frequency to transmit data over the closely-coupled wireless link 727, where the second frequency is different from the first frequency. During the data transmission, the external resonant circuit 740 and the implantable resonant circuit 742 both remain tuned to the first frequency (i.e., the external resonant circuit 740 and the implantable resonant circuit 742 each have a fixed structure that fixes the tuned frequency thereof). As such, the frequency "mismatch" or difference between the transmit frequency and the frequency of the resonant system 750 causes a reduction in the quality factor of the combined resonant system (i.e., reduces the quality factor of the closely-coupled wireless link 727), which in turn increases the bandwidth available for the transmission of the data.

In summary, FIG. 7 illustrates an arrangement in accordance with embodiments presented herein in which, during a first set of time periods, the external resonant circuit 740, which includes external coil 706, is driven at a first frequency to transmit power to the implantable resonant circuit 742, including implantable coil 722. During a second set of time periods, the external resonant circuit 740 is driven at a second frequency to transmit data to the implantable resonant circuit 742, where the second frequency is frequency spaced a frequency distance from the first frequency. During both the first and second sets of time periods, the external resonant circuit 740 and the implantable resonant circuit 742 remain tuned to the first frequency (i.e., the external resonant circuit 740 and the implantable resonant circuit 742 have a fixed tuning).

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device, comprising:
    an implantable resonant circuit comprising an implantable coil;
    an external resonant circuit comprising an external coil configured to transcutaneously transfer power and data to the implantable resonant circuit using separate power and data time slots, respectively; and
    external radio-frequency (RF) interface circuitry configured to drive the external resonant circuit at a first frequency during the power time slots and to drive the external resonant circuit at a second frequency during the data time slots, wherein the second frequency is different from the first frequency.

2. The implantable medical device of claim 1, wherein the implantable resonant circuit and the external resonant circuit each have a fixed resonant frequency that does not change during either of the power or the data time slots.

3. The implantable medical device of claim 2, wherein the fixed resonant frequencies of the implantable resonant circuit and the external resonant circuit are substantially the same as the first frequency.

4. The implantable medical device of claim 1, wherein a physical arrangement of each of the implantable resonant circuit and the external resonant circuit remains fixed during each of the power and the data time slots.

5. The implantable medical device of claim 1, wherein the first frequency is selected based on a resonant frequency of each of the implantable resonant circuit and the external resonant circuit and is a frequency that corresponds to a predetermined power coupling between the external resonant circuit and the implantable resonant circuit.

6. The implantable medical device of claim 5, wherein the predetermined power coupling is a substantially maximum power coupling between the external resonant circuit and the implantable resonant circuit.

7. The implantable medical device of claim 5, wherein the predetermined power coupling is a non-optimized power coupling between the external resonant circuit and the implantable resonant circuit.

8. The implantable medical device of claim 1, wherein the first frequency provides a selected power coupling between the external resonant circuit and the implantable resonant circuit, and wherein the second frequency is frequency spaced from the first frequency so as to provide a selected bandwidth for transfer of data to the implantable coil during the data time slots.

9. The implantable medical device of claim 1, wherein the second frequency is spaced from the first frequency by a predetermined frequency distance.

10. The implantable medical device of claim 1, further comprising:
- a control circuit coupled to the implantable resonant circuit, wherein the control circuit is configured to:
- identify a maximum power coupling between the external resonant circuit and the implantable resonant circuit; and
- set a resonant frequency of the implantable resonant circuit based on the identified maximum power coupling.

11. The implantable medical device of claim 10, wherein the implantable resonant circuit comprises one or more variable capacitance components, and wherein the control circuit is configured to adjust the capacitance of the one or more variable capacitance components to set the resonant frequency of the implantable resonant circuit based on the resonant frequency of the external resonant circuit.

12. The implantable medical device of claim 10, wherein the control circuit is configured to set the resonant frequency of the implantable resonant circuit to a frequency that is substantially the same as the resonant frequency of the external resonant circuit.

13. The implantable medical device of claim 1, wherein the first frequency is selected based on a resonant frequency of each of the implantable resonant circuit and the external resonant circuit and is a frequency that corresponds to a non-optimized power coupling between the external resonant circuit and the implantable resonant circuit.

14. The implantable medical device of claim 1, wherein the second frequency is a multiple of the first frequency.

15. The implantable medical device of claim 1, wherein the second frequency is a division of the first frequency.

* * * * *